(12) United States Patent
Kikuchi et al.

(10) Patent No.: US 6,787,770 B2
(45) Date of Patent: Sep. 7, 2004

(54) METHOD OF INSPECTING HOLES USING CHARGED-PARTICLE BEAM

(75) Inventors: Naoki Kikuchi, Tokyo (JP); Tsutomu Negishi, Tokyo (JP); Yuki Ono, Tokyo (JP)

(73) Assignee: JEOL Ltd., Tokyo (JP)

( * ) Notice: Subject to any disclaimer, the term of this patent is extended or adjusted under 35 U.S.C. 154(b) by 37 days.

(21) Appl. No.: 10/060,944

(22) Filed: Jan. 30, 2002

(65) Prior Publication Data

US 2003/0104639 A1 Jun. 5, 2003

(30) Foreign Application Priority Data

Jan. 30, 2001 (JP) ........................................ 2001-021615

(51) Int. Cl.[7] .............................................. G01N 23/04
(52) U.S. Cl. ...................... 250/307; 250/307; 250/310; 250/311; 250/396 R; 250/397; 250/440.11; 250/442
(58) Field of Search ................................. 250/307, 310, 250/311, 396 R, 396 ML, 397, 440.11, 442

(56) References Cited

FOREIGN PATENT DOCUMENTS

GB    2338297    12/1999

OTHER PUBLICATIONS

Matsui et al. "Wafer Inspection System and Wafer Inspection Process Using Charged Particle Beam", Pub. No.: US 2002/0134936 A1, publication date: Sep. 26, 2002.*

Ishimoto et al. "Method of Inspecting Holes Using Charged–Particle Beam", Pub. No.: 2001/0022345 A1, published Sep. 20, 2001.*

Yamada et al. "Semiconductor Device Inspection Apparatus", Pub. No.: US 2002/0070738 A1, published Jun. 13, 2002.*

* cited by examiner

Primary Examiner—John R. Lee
Assistant Examiner—Zia R. Hashmi
(74) Attorney, Agent, or Firm—Webb Ziesenheim Logsdon Orkin & Hanson, P.C.

(57) ABSTRACT

This disclosure is directed to a method of inspecting how contact holes or via holes are formed in a sample, such as a wafer. An electron beam is directed to the contact holes in succession. An absorbed current flowing through the sample is detected by a current amplifier. Data about the obtained absorbed current is stored in a memory. The electric current flowing through a reference sample and ground is measured, and the relation of the current to the etch depths of contact holes into the substrate is previously found. A control unit compares data about the measured current with the previously found relation and determines the depths of holes of interest into the substrate (i.e., inspects how they are etched).

20 Claims, 9 Drawing Sheets

(a)

(b)

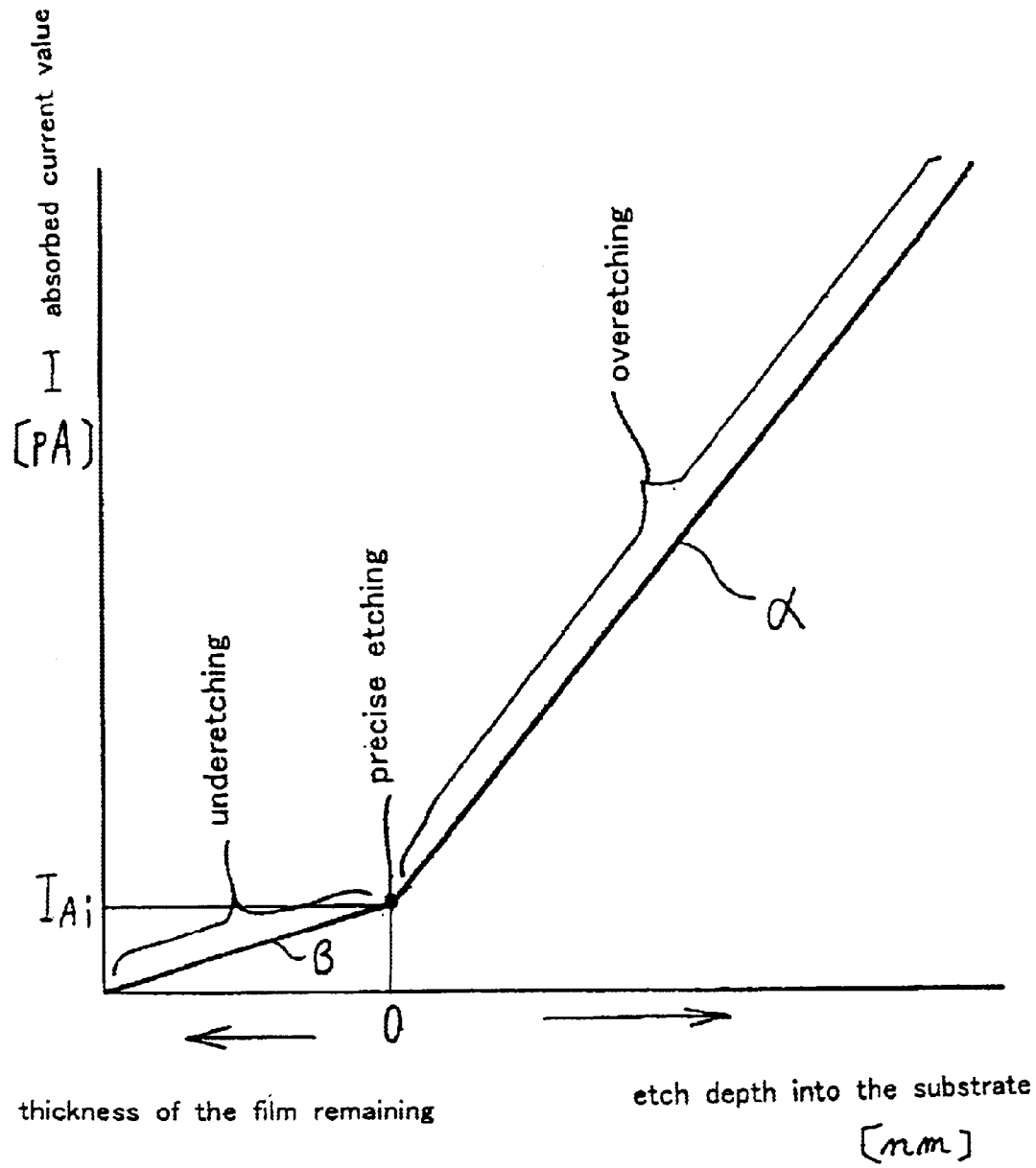

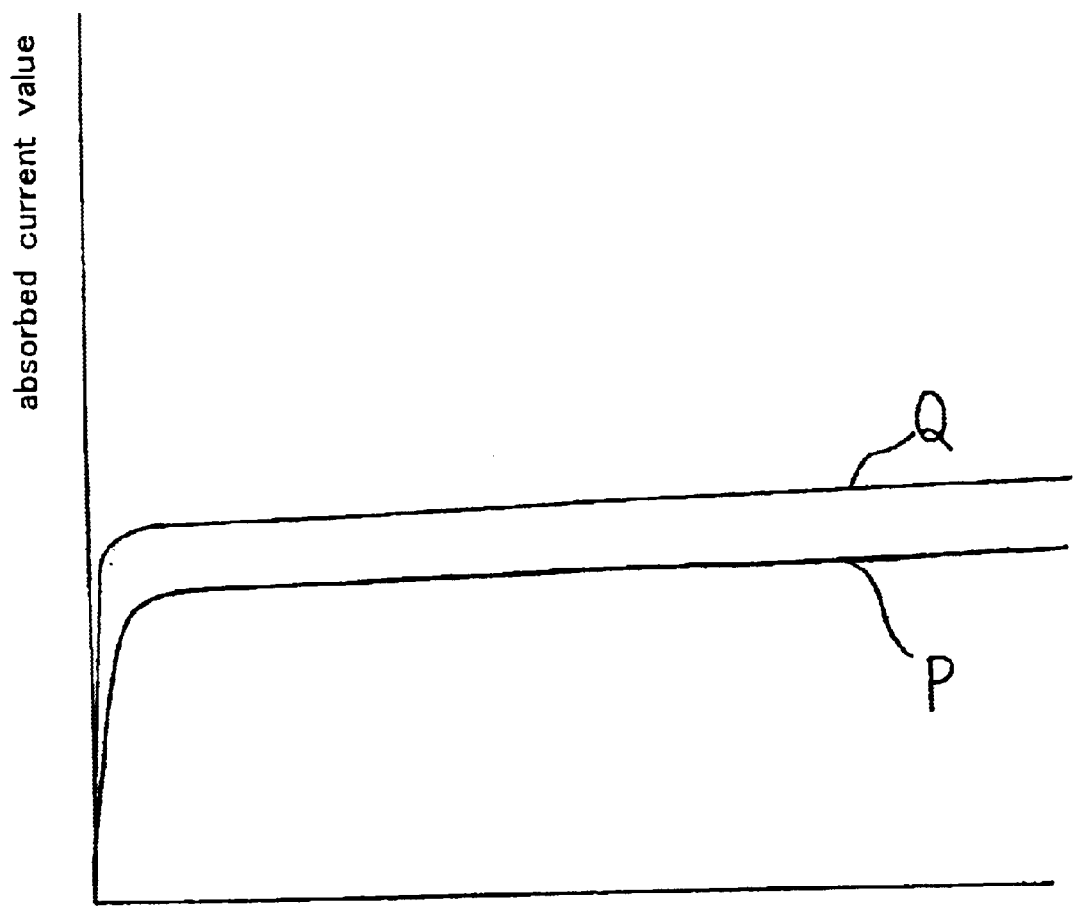

METHOD OF INSPECTING HOLES USING CHARGED-PARTICLE BEAM

BACKGROUND OF THE INVENTION

1. Field of the Invention

The present invention relates to a method of inspecting holes, such as contact holes or via holes, using a charged-particle beam, the holes being forming during a manufacturing process for semiconductor devices, such as ICs and LSIs, to understand the state of formed holes, especially the state of etched holes.

2. Description of the Related Art

A semiconductor device consists, for example, of a silicon wafer (silicon substrate) on which a multilayer structure is formed. In this multilayer structure, a dielectric layer is formed between certain layers. Contact holes or via holes are formed in this dielectric layer. These contact holes or via holes are filled by metallization (with conductive material) to make electrical connections between the certain layers. In the following description, contact holes are taken as an example.

Such contact holes are formed by applying resist to the dielectric layer, exposing the resist according to the pattern of the contact holes, and then performing development and etching steps during a process for fabricating a semiconductor device.

Where these contact holes are formed, if a contact hole Ca extends even somewhat into a conductive layer D through a dielectric layer A (known as overetching) as shown in FIG. 1(a), or if a contact hole Cb is formed while leaving behind a part of the dielectric layer A (known as underetching), the final product does not function normally as a semiconductor device and is a defective device.

Therefore, inspecting the state of the contact holes after they have been formed is important in determining whether the subsequent process sequence is to be carried out or not. Furthermore, it can be judged according to the results of this inspection (i.e., the state of the formed contact holes) whether the development or etching that is a previous step was appropriate or not. Additionally, the process for forming the contact holes can be analyzed for causes of defects.

The state of contact holes formed in this way is inspected nondestructively, for example, by electron beam irradiation from a scanning electron microscope (SEM). In particular, contact holes are scanned with an electron beam. A secondary electron image of the contact holes is displayed on the viewing screen of a display unit, based on detected secondary electrons. This image is observed. Thus, the state of the etched contact holes (i.e., the etching process) is inspected (see, for example, Great Britain Patent No. 2338297A).

In recent years, elements forming semiconductor devices have become decreased in size. Also, these elements have tended to be formed in plural layers. With this trend, contact hole diameters have decreased. Also, their depths have increased. Consequently, contact holes have increased in aspect ratio (depth/diameter). Therefore, the efficiency at which secondary electrons from inside holes are captured has decreased greatly. This has made it difficult to precisely determine the state of formed contact holes, i.e., the etching process.

In some cases, a wafer is cut along a plane including the center axis of a contact hole, and the cross section is observed with an SEM. In recent years, however, larger wafer sizes (e.g., having diameters of 200 to 300 mm) have been used. Therefore, it is difficult to create cross sections adapted for observation with an SEM. Furthermore, the aspect ratio (depth/diameter) of contact holes has tended to increase as mentioned previously, thus making it difficult to perform the cutting operation itself for cutting a wafer along a plane including the center axis of a contact hole.

A method of evaluating the thickness of a film remaining on the bottom surface of a contact hole has been recently proposed. An electron beam is made to hit this contact hole having the remaining film on its bottom surface. The value of an electric current flowing through the remaining film into a support substrate located immediately under the opening is measured. A pseudo-remaining film on the bottom surface of the opening is assumed. A reference sample is used to previously create a comparison table that correlates the aforementioned current value with the thickness of the pseudo-remaining film. Then, an electron beam is directed to a contact hole to be inspected. The value of the current passing through the film is measured. The thickness of the film remaining on the bottom surface of the contact hole is evaluated based on the measured current value by referring to the comparison table. This method is only capable of evaluating the thickness of the film remaining on the bottom surface of the contact hole.

Where contact holes are formed during a process for fabricating semiconductor devices, underetching may occur, leaving behind a film in contact holes. In practice, overetching may also take place. That is, contact holes extend into the substrate. In the latter case, it is necessary to determine the depth of the contact holes into the substrate (i.e., etch depth of the contact holes into the substrate) based on results of an inspection of the contact holes.

SUMMARY OF THE INVENTION

It is an object of the present invention to provide a novel method of inspecting a contact hole or holes using a charged-particle beam in such a way that the state of the contact holes can be grasped (i.e., it is possible to know how the holes are etched).

A method of inspecting a hole using a charged-particle beam in according with the present invention comprises the steps of: irradiating the hole with the charged-particle beam, the hole being formed in an etched layer on a substrate forming a sample to be inspected; detecting an electric current flowing between the inspected sample and ground as a result of the irradiation; and finding the etch depth of the hole into the substrate regarding the inspected sample, based on a relation of the current flowing between a reference sample and ground to the etch depth of the hole into the substrate, the relation being previously found using the reference sample.

Another method of inspecting a hole using a charged-particle beam in accordance with the present invention comprises the steps of: irradiating the hole with the charged-particle beam, the hole being formed in an etched layer on a substrate forming a sample to be inspected; detecting an electric current flowing between the inspected sample and ground as a result of the irradiation; and finding how the hole in the inspected sample is etched, based on a relation of the current flowing between a reference sample and ground to etch depths of holes into the substrate and on a relation of the current to remaining film thickness in the holes, the relations being previously found using the reference sample.

A further method of inspecting a hole using a charged-particle beam in accordance with the present invention comprises the steps of: irradiating the hole with the charged-particle beam, the hole being formed in an etched layer on a substrate forming a sample to be inspected; detecting an electric current flowing between the inspected sample and ground as a result of the irradiation; comparing the detected current with a reference electric current previously found from a precisely etched reference sample, the reference electric current flowing between the reference sample and ground; and judging that the hole in the inspected sample has been precisely etched if the two compared currents are the same, that the hole has been overetched if the former current is greater than the latter current, and that the hole has been underetched if the former current is smaller than the latter current.

Yet another method of inspecting holes using a charged-particle beam in accordance with the present invention comprises the steps of: irradiating a region containing the holes with the charged-particle beam, the holes being formed in an etched layer on a substrate forming a sample to be inspected; detecting an electric current flowing between the inspected sample and ground as a result of the irradiation; repeating these steps for plural regions previously established on the inspected sample; obtaining data about the distribution of etch depths of holes in the inspected sample into the substrate, based on the detected current and on a relation of a reference current to etch depths of holes into the substrate, the reference current flowing between a reference sample and ground, the relation being previously found using the reference sample; and displaying a map based on the obtained data about the distribution on a display unit.

Still another method of inspecting holes using a charged-particle beam comprises the steps of: irradiating a region containing the holes with the charged-particle beam, the holes being formed in an etched layer on a substrate forming a sample to be inspected; detecting an electric current flowing between the inspected sample and ground as a result of the irradiation; repeating these steps for plural regions previously established on the inspected sample; obtaining data about the distribution of etch depths of the holes in the inspected sample into the substrate, based on a previously found relation of electric current flowing between the reference sample and ground to etch depths of holes into the substrate and on a previously found relation of the electric current to remaining film thickness in the holes; and displaying a map on a display unit, based on data obtained about the distribution of degrees of etching in the holes in the inspected sample.

An additional method of inspecting holes using a charged-particle beam in accordance with the present invention comprises the steps of: preparing a reference sample precisely etched; preparing an unknown sample that is not known whether it has been etched precisely or not; irradiating a region of the reference sample containing holes with the charged-particle beam; detecting an electric current flowing between the reference sample and ground; repeating these irradiating and detecting steps for previously established plural regions on the reference sample; irradiating a region of the known sample containing holes with the charged-particle beam; detecting an electric current flowing between the unknown sample and ground; repeating these irradiating and detecting steps for previously established plural regions on the unknown sample; finding data about current distributions on the reference and unknown samples; creating graphs indicative of the characteristics of the currents flowing through the regions of the reference sample and unknown sample; and displaying the graphs side by side on a display unit.

Other objects and features of the invention will appear in the course of the description thereof, which follows.

DESCRIPTION OF THE PREFERRED EMBODIMENTS

Before describing the preferred embodiments of the present invention with reference to the accompanying drawings, the principle of the present invention is described. Where a semiconductor device is inspected in accordance with the present invention, it is judged based on an absorbed current whether a contact hole has been overetched, underetched, or precisely etched. An electric current (absorbed current) flows into the semiconductor substrate (conductive layer) through the bottom of the contact hole. Where the contact hole has been precisely etched, it follows that no dielectric layer is left at the bottom of the contact hole and that the substrate is left unetched.

The incident electron current Ia based on an electron beam hitting the contact hole, the absorbed current Ib, and the current Ic of reflected electrons including secondary electrons have the relation:

$$Ia=Ib+Ic$$

Figures 2A, 2B, 2C:
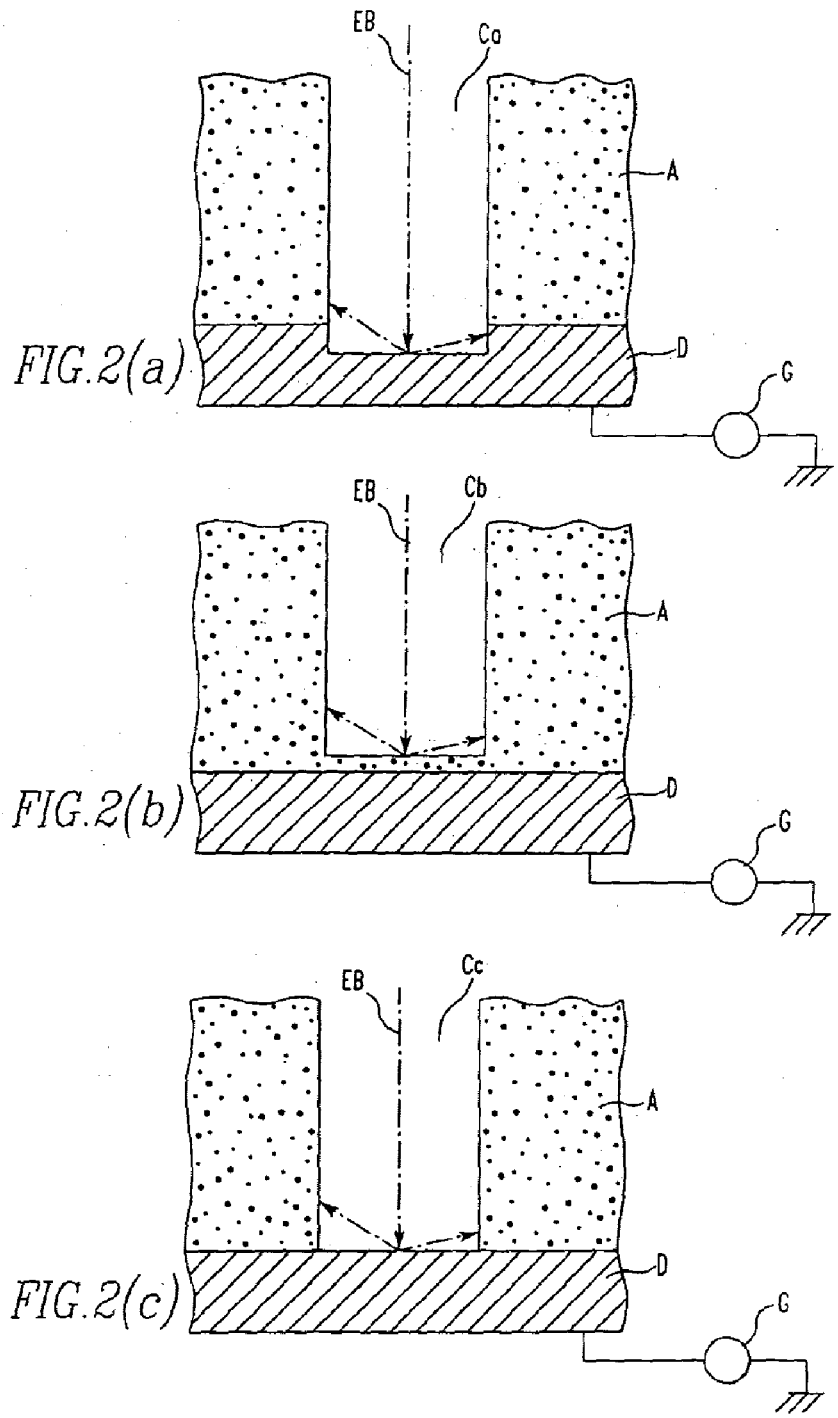
Figure 3:
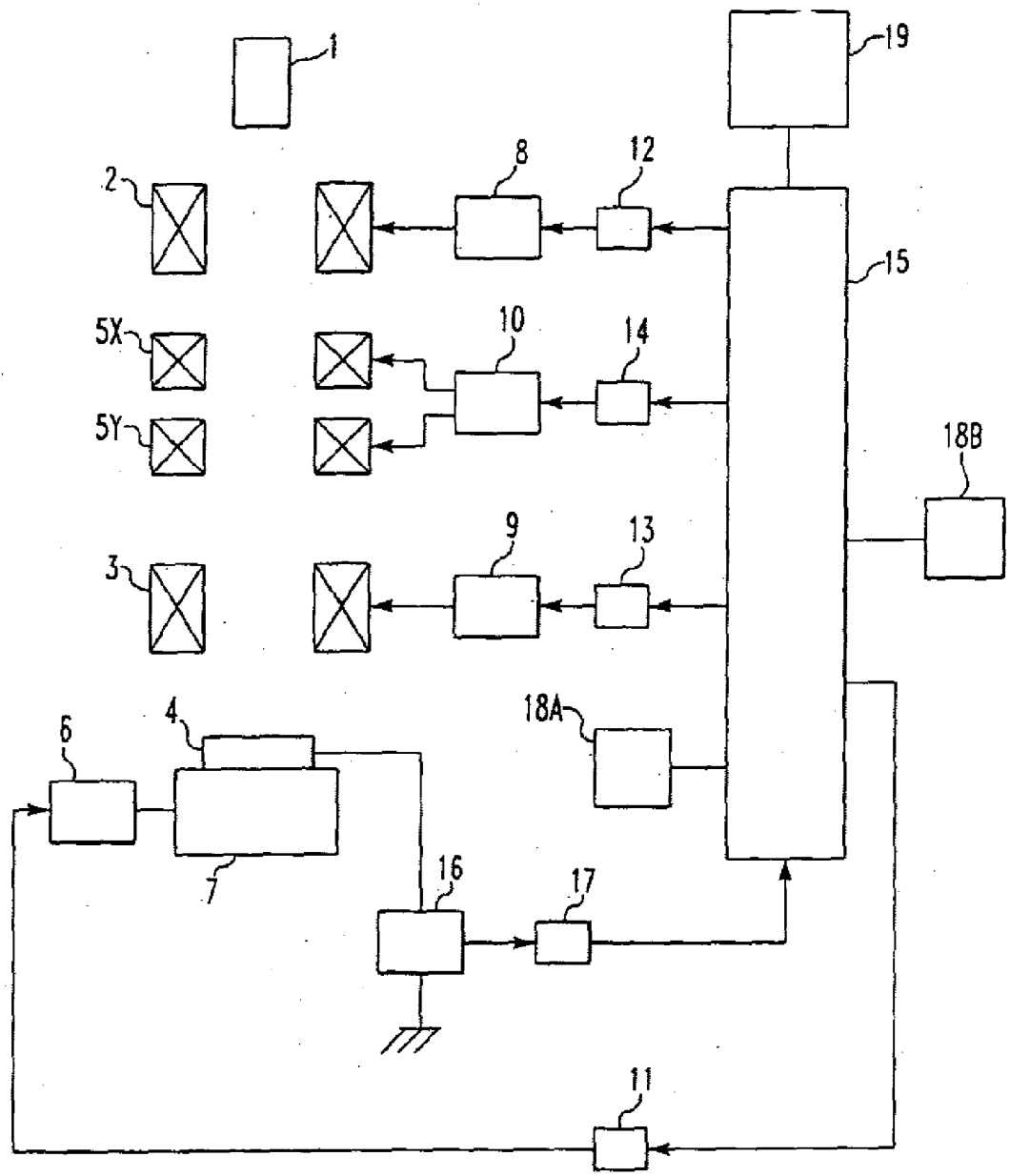

In the case of a contact hole (Cc of FIG. 2(c)) precisely etched, if electrons EB hit the bottom surface (the surface of a conductive layer D) of the contact hole Cc, some are absorbed into the bottom surface of the contact hole Cc, whereas the others are reflected. If these reflected electrons partially reach the side surface of the contact hole Cc, no absorbed current flows because the side surface is entirely made of the inner surface of a dielectric layer A. Accordingly, the current detected by an ammeter G arises only from electrons absorbed into the bottom surface of the contact hole Cc.

In the case of an overetched contact hole (Ca of FIG. 2(a)), if electrons EB hit the bottom surface (the surface of the conductive layer D) of the contact hole Ca, some are absorbed into the bottom surface of the hole Ca, while the others are reflected. Some of the reflected electrons reach the side surface of the contact hole Ca. This side surface is composed of the inner surface of the dielectric layer A and the inner surface of the conductive layer D. If electrons reach the former inner surface, no absorbed current flows. If electrons reach the latter inner surface, some of the electrons are absorbed. Therefore, the current detected by the ammeter G arises from electrons absorbed into the bottom surface of the contact hole Ca and from electrons absorbed into the conductive layer of the side surface. Hence, this current is larger than the current occurring where the hole is precisely etched. We have confirmed that the degree of the difference roughly corresponds to the area of the conductive layer that occupies a part of the area of the side surface of the contact hole Ca.

In this way, there is a correlation between the state of each etched contact hole (i.e., the etch depth into the substrate) and the total area of the conductive layer portions exposed at the bottom and side surfaces of the contact hole. That is, the state of the formed contact hole (i.e., the etch depth of the contact hole into the substrate) has a close relation with the magnitude of the absorbed current arising from the detected electrons. Accordingly, a silicon wafer (reference sample) having contact holes overetched to known different degrees is previously prepared. An electron beam is made to hit each contact hole. The resulting absorbed current is measured. Based on these measurements, the relation of the absorbed current value to the etch depth of the contact hole into the substrate is found. An electron beam is caused to hit a contact hole that is a sample to be investigated. The resulting absorbed current is measured. The measured current is compared with the above-described relation. Consequently, the state of the etched hole, or the etch depth of the contact hole, which is a sample under investigation, into the substrate, can be evaluated.

Figure 1:
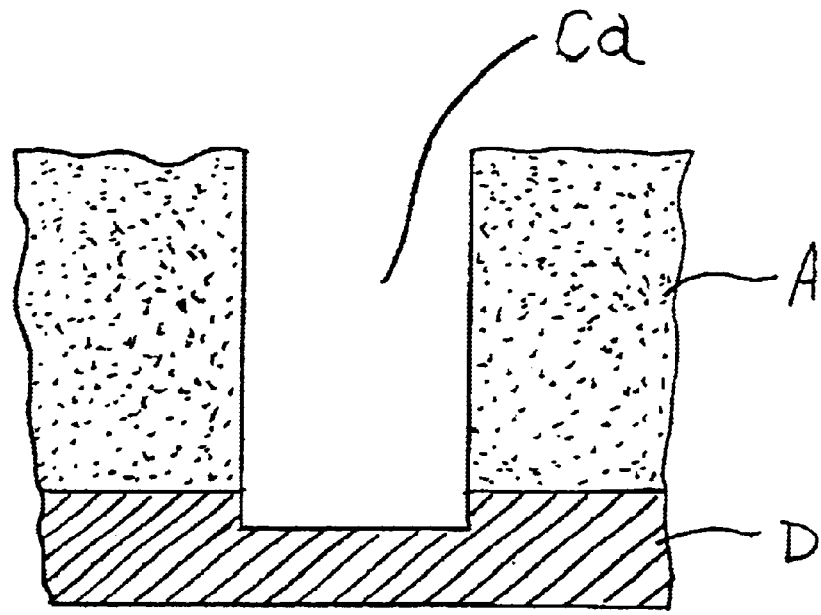
FIGS. 1(a) and 1(b) are fragmentary cross sections of contact holes showing how they have been etched.
Figure 1:
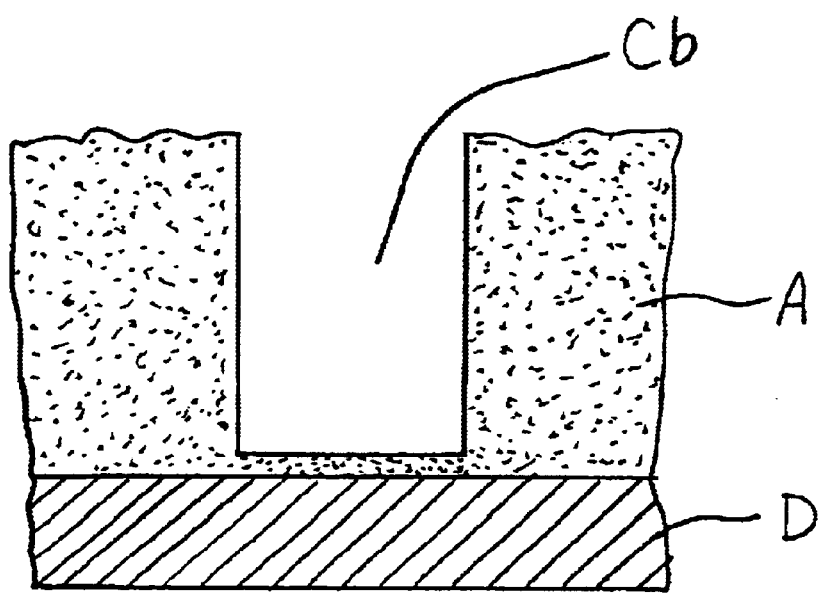
Figure 2:
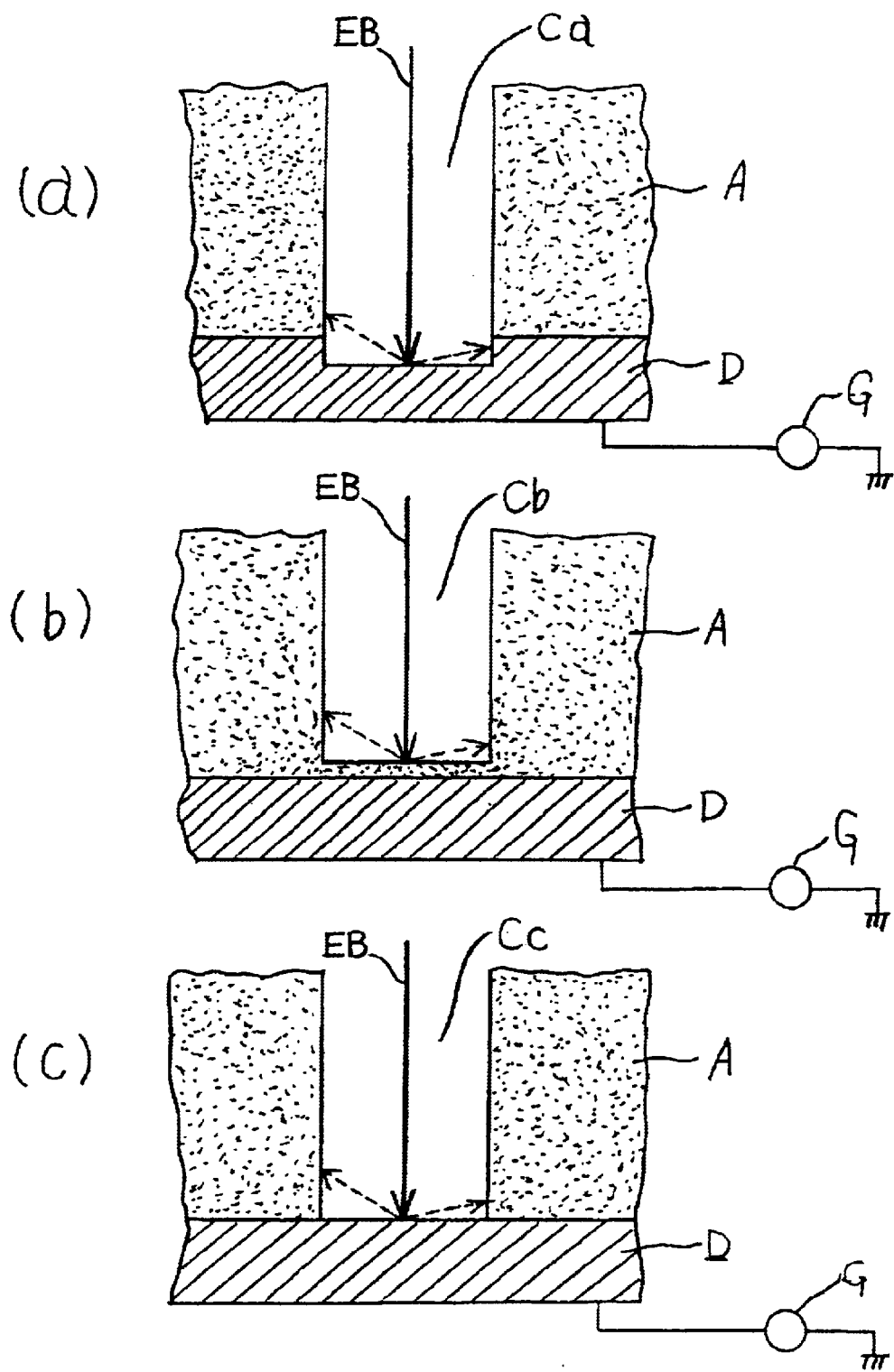
FIGS. 2(a), 2(b), and 2(c) are fragmentary cross sections of contact holes, and in which an electron beam is directed to the bottom surfaces of the contact holes.
Figure 3:
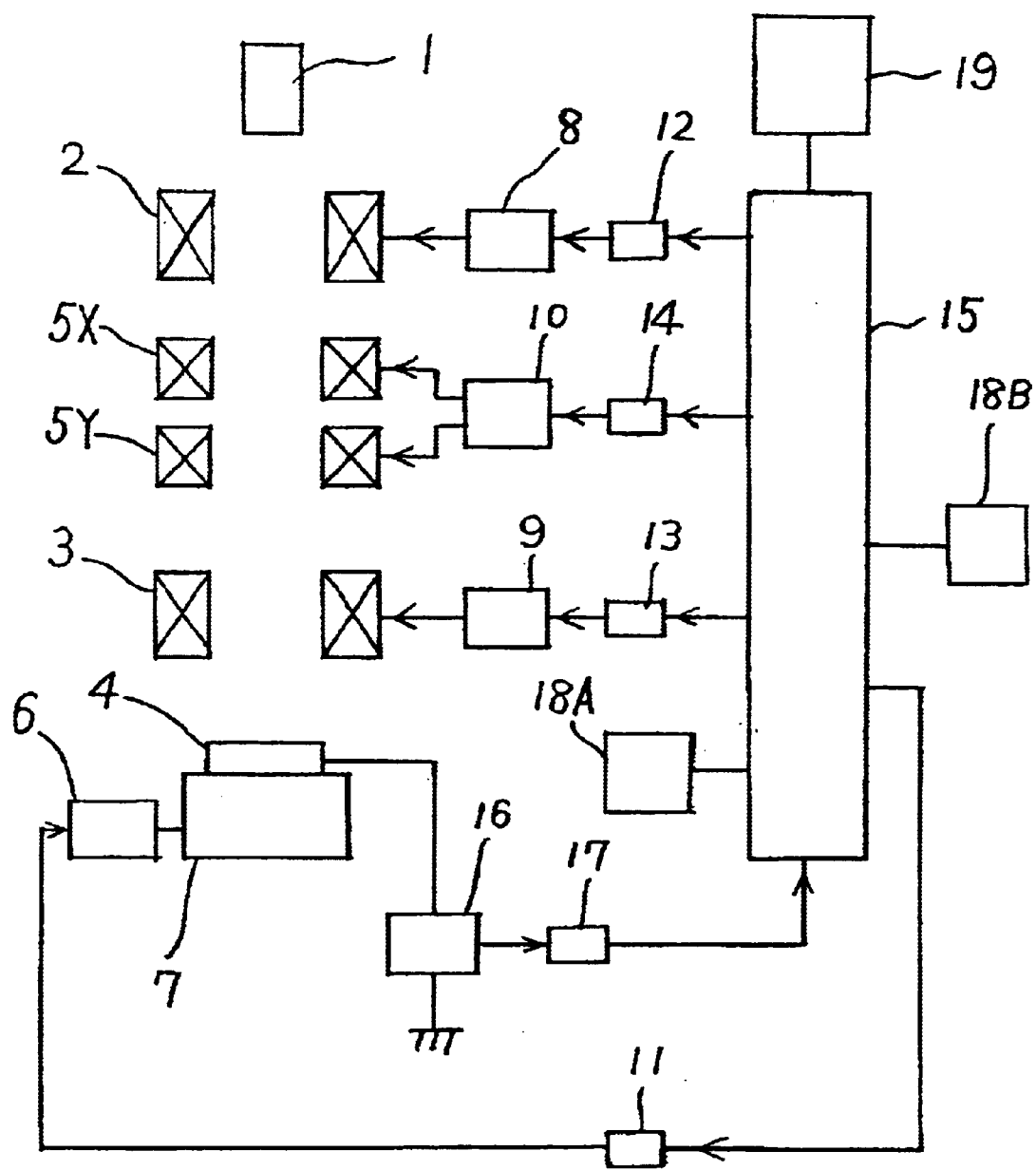
FIG. 3 is a schematic block diagram of one example of inspection equipment for carrying out a method of inspecting semiconductor devices in accordance with the present invention.

FIG. 3 schematically shows one example of inspection equipment for carrying out a method of inspecting a semiconductor device in accordance with the present invention. An electron gun 1 emits an electron beam that is appropriately focused onto a sample 4, such as a wafer, by a system of condenser lenses 2 and an objective lens 3. An X-deflection coil 5X and a Y-deflection coil 5Y cause the electron beam to scan across the sample 4. The sample 4 is placed on a sample stage 7 that is moved by a stage drive mechanism 6. A lens control circuit 8 controls the excitation strength of the system of condenser lenses 2. Another lens control circuit 9 controls the excitation strength of the objective lens 3. A deflection control circuit 10 supplies deflecting signals to the deflection coils 5X and 5Y. A sample stage moving instruction, a lens controlling instruction, and a deflection controlling instruction are sent from a control unit 15 to the stage drive mechanism 6, lens control circuits 8, 9, and deflection control circuit 10 via D/A converters 11, 12, 13, and 14, respectively. The control unit 15 gives various instructions and performs various kinds of data processing.

A current amplifier 16 detects the current (absorbed current) flowing through the sample 4 and amplifies the current. The output from the current amplifier 16 is sent to the control unit 15 via an A/D converter 17. Two memories 18A and 18B are connected with the control unit 15. A display unit 19 consists of a cathode-ray tube (CRT) or the like.

In this instrument, data ($I_{Ai}$ in FIG. 4) about absorbed current values where a contact hole has been precisely etched is previously stored in the memory 18B. The current values are measured using the reference sample.

The electron beam from the electron gun 1 is appropriately focused by the system of condenser lenses 2 and objective lens 3. The electron beam is directed onto a contact hole of interest in the sample 4 by the deflection coils 5X and 5Y. The absorbed current flowing through the sample 4 is detected and amplified by the current amplifier 16. The output signal from this amplifier 16 is sent to the control unit 15 via the A/D converter 17. The control unit 15 holds data about this absorbed current in the memory 18A.

The control unit 15 reads data $I_{Ai}$ about absorbed current values from the memory 18B where the hole has been precisely etched. The control unit 15 also reads data about the absorbed current signals just measured from the memory 18A. If the measured absorbed current is the same as the absorbed current value $I_{Ai}$, the control unit judges that the inspected contact hole has been precisely etched. If the measured absorbed current value is greater than the absorbed current value $I_{Ai}$, then the control unit 15 judges that the contact hole has been overetched. If the measured absorbed current value is smaller than the absorbed current value $I_{Ai}$, then the control unit 15 judges that the contact holes have been underetched. The results of the judgment are displayed on the display unit 19. For example, if the hole has been precisely etched, symbol "O" is displayed. If the hole has been overetched, symbol "X" is displayed. If the hole has been underetched, symbol "Δ" is displayed. Alternatively, precise etching, overetching, and underetching may be displayed in green, red, and blue, respectively. The hole is judged to be etched precisely if the absorbed current falls within a range $I_{Ai} \pm \Delta I$ (where $\Delta I$ is a tight tolerance).

Measurements on one contact hole can be performed and the results of the judgment can be displayed as described above. This sequence of operations is performed for contact holes at arbitrary positions on the sample 4. Consequently, it is possible to judge the state of each etched contact hole, i.e., whether each contact hole has been precisely etched.

In the description given above, the absorbed current value $I_{Ai}$ indicating that each hole has been precisely etched is stored in the memory 18B. Only a decision is made based on this value $I_{Ai}$ as to whether the hole has been overetched, precisely etched, or underetched.

In the following embodiment, the degree of overetching (i.e., the etch depth into the substrate) can be known. In addition, in this embodiment, in case of underetching, the degree of underetching, i.e., the thickness of the film remaining in the contact hole, can be known. Accordingly, in this embodiment, the state of the etched hole can be known. Furthermore, the degree of the etching can be evaluated precisely, whether the hole has been overetched or underetched.

Figure 4:
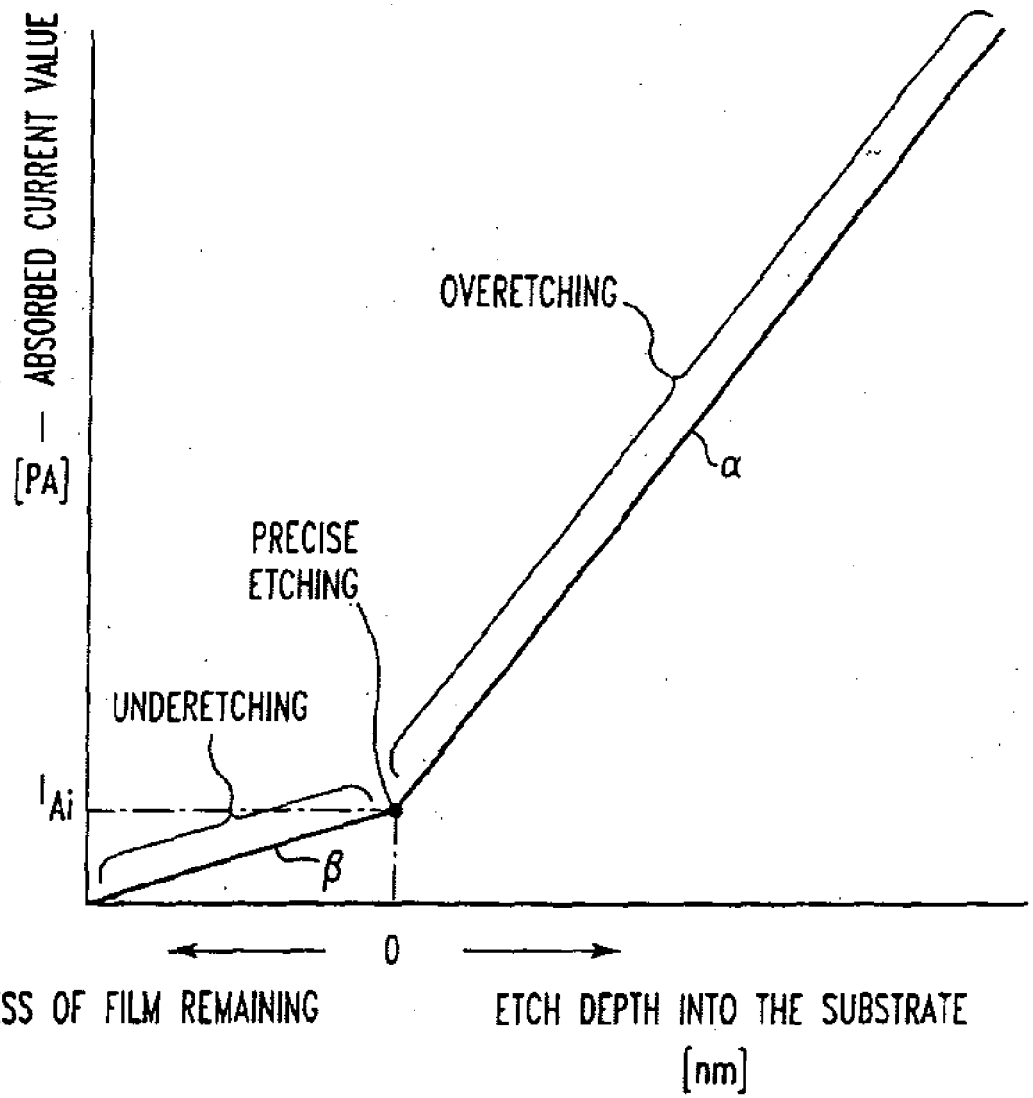
FIG. 4 is a graph showing the relation among the value of absorbed current, the etch depth of each contact hole into a substrate, and the thickness of residual film.
Figure 5:
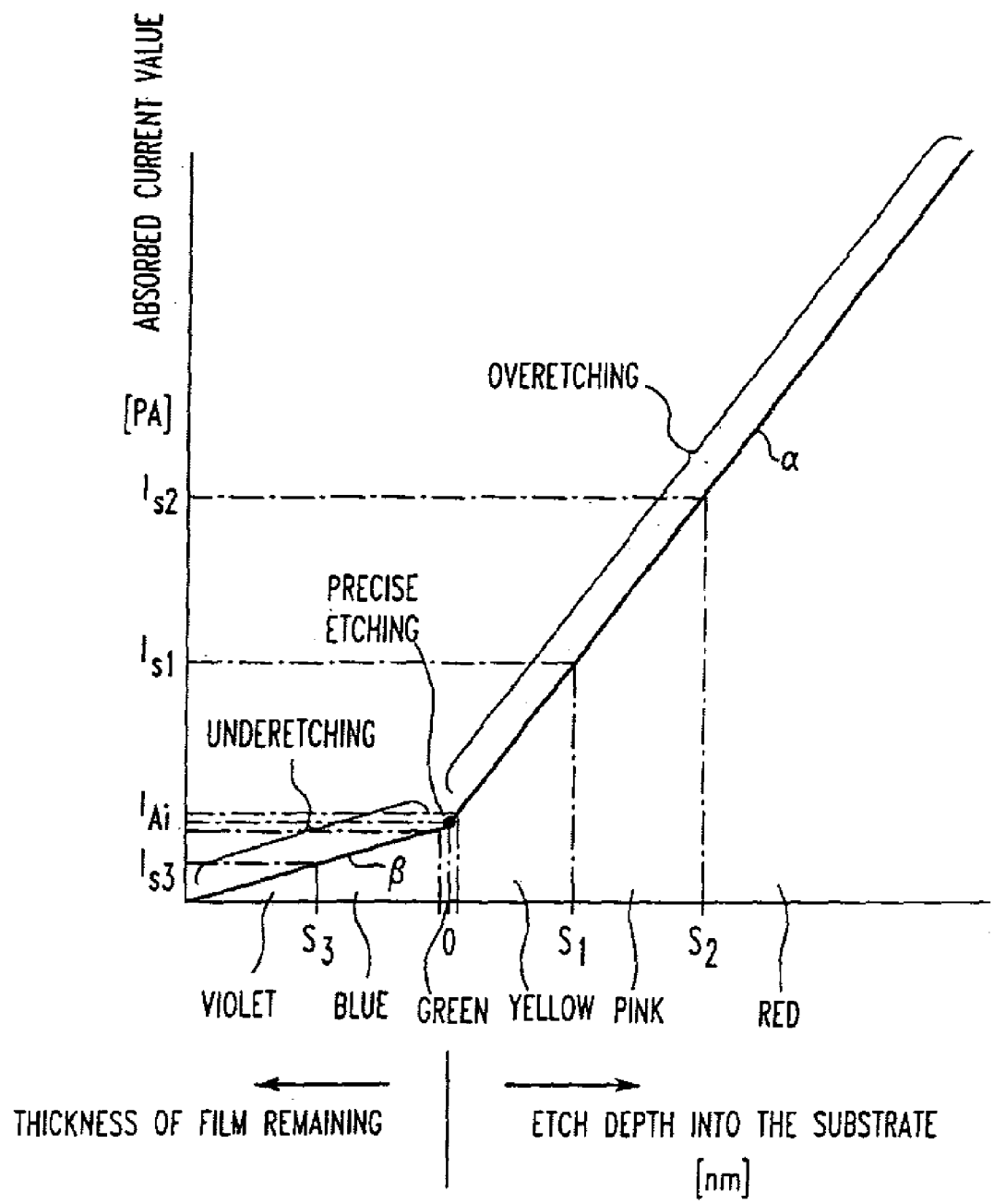
Figure 6:
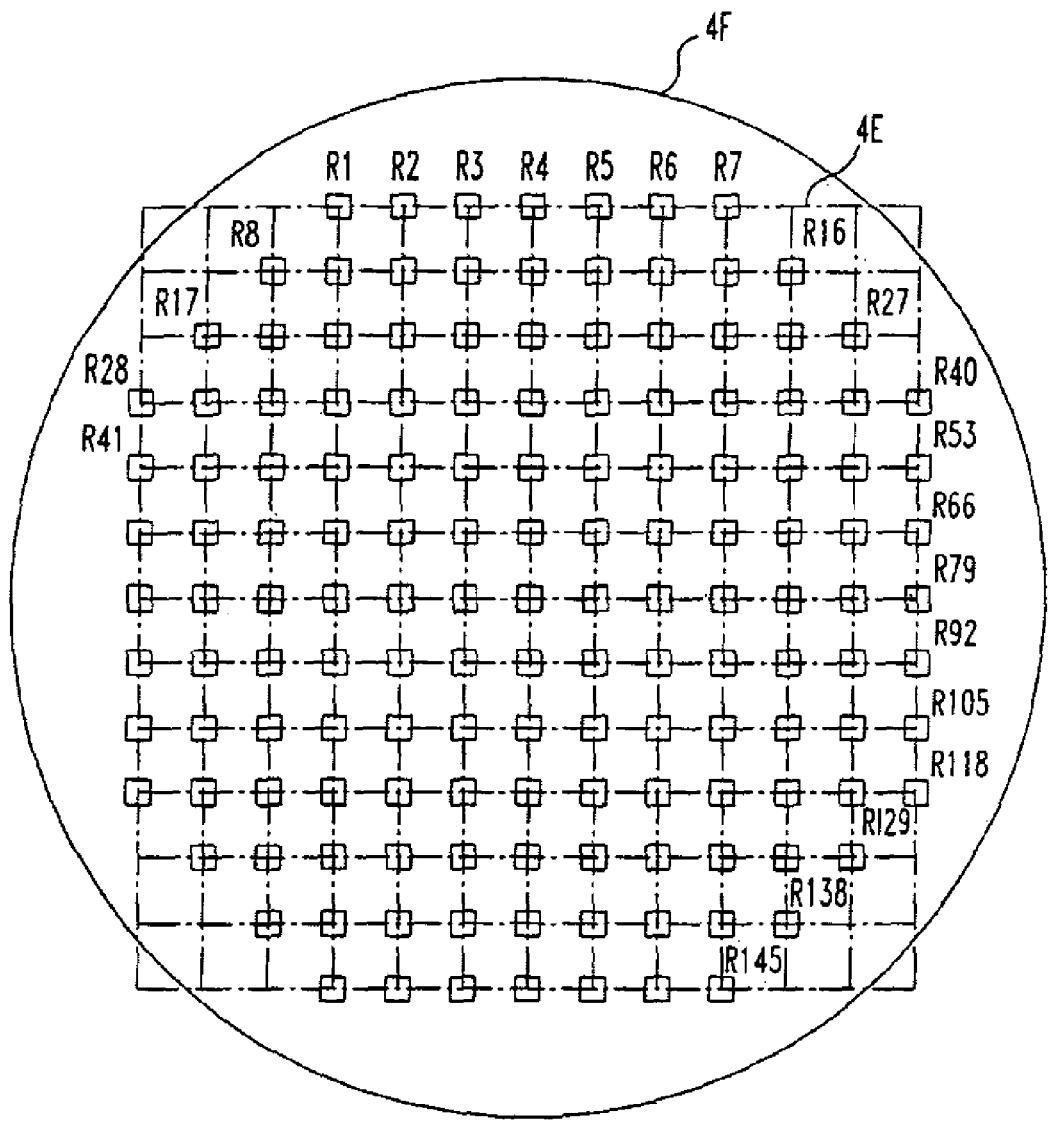
Figure 7:
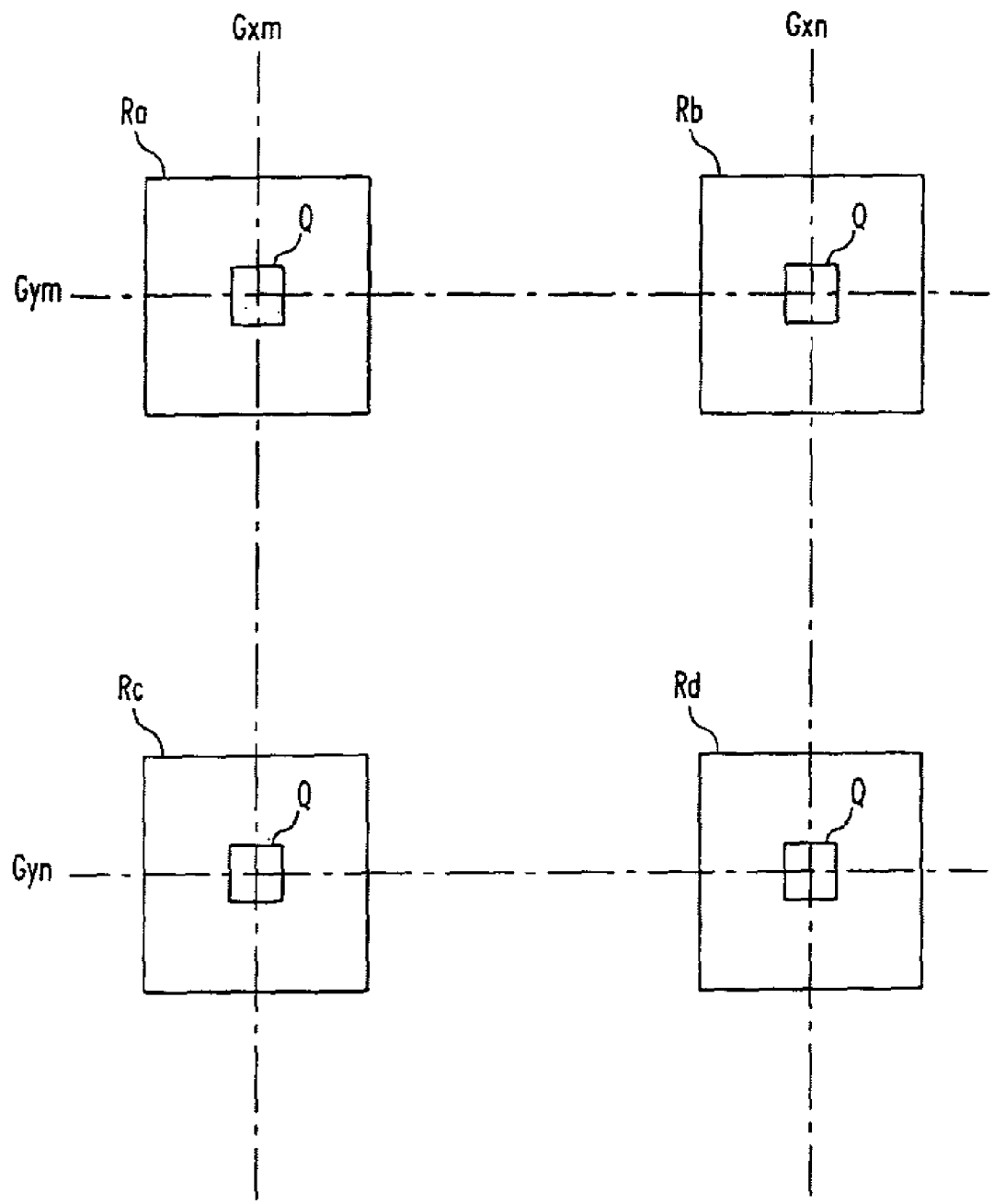
Figure 8:
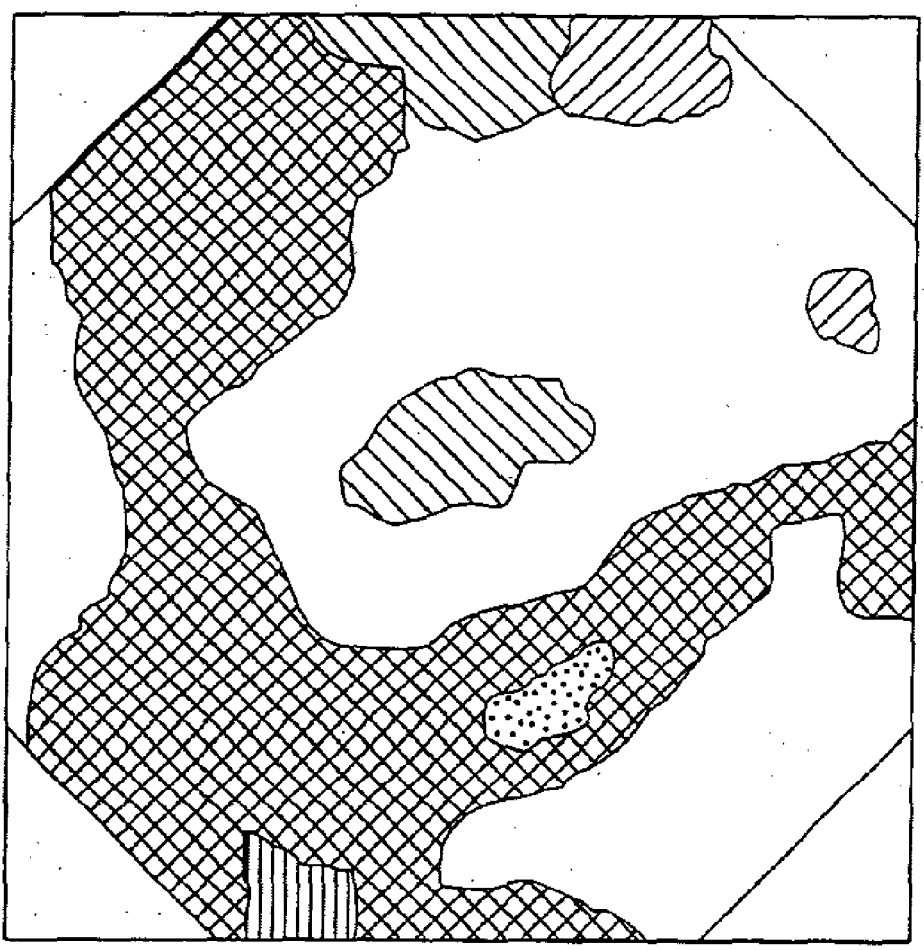
Figure 8:
Figure 8:
Figure 8:
Figure 8:
Figure 8:
Figure 8:

First, the relation (α of FIG. 4) of the absorbed current value I to the etch depth of the contact hole into the substrate and the relation (β of FIG. 4) between the thickness of the film remaining in the contact hole and the absorbed current value I are found, using a reference sample. A reference table for absorbed current value-etch depth conversion and for absorbed current value-remaining film thickness conversion as shown in FIG. 4 is stored in the memory 18B.

Then, an electron beam is directed to one desired contact hole in the inspected sample 4. Data about an absorbed current signal obtained from the inspected sample 4 is stored in the memory 18A.

Figure 5:
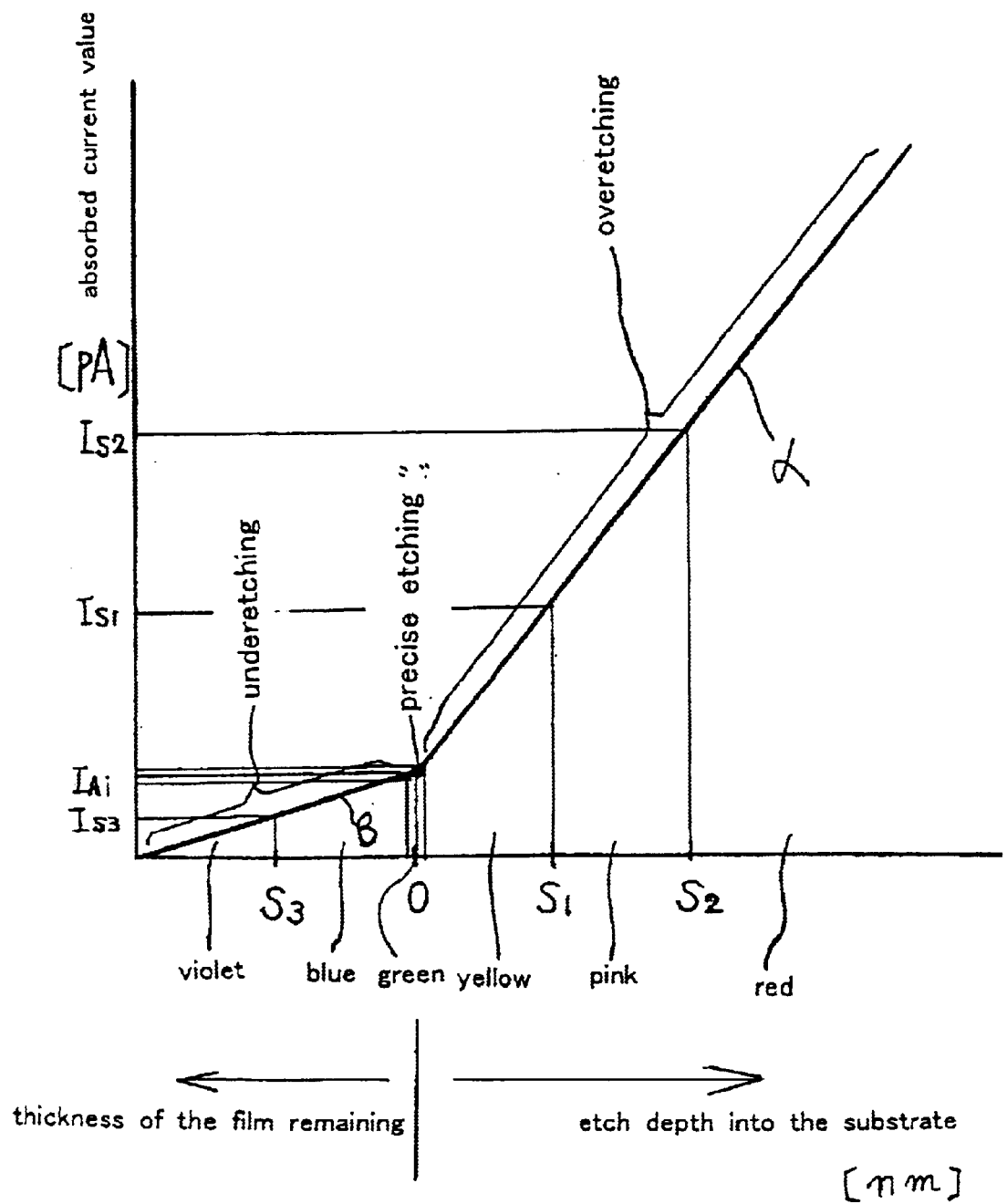
FIG. 5 is a graph in which the range of absorbed current is classified according to the degree of etching where the relation shown in FIG. 4 holds.

After this measurement, the control unit 15 compares each absorbed current signal value stored in the memory 18A with absorbed current values stored in the memory 18B and finds the value of etch depth or remaining film thickness corresponding to the absorbed current signal value. In displaying the found etch depth or remaining film thickness, the degree of the etching may be displayed using different colors or symbols, such as numerals. For example, the range of etch depth in the overetched area α into the substrate is divided into three subranges, for example, as shown in FIG. 5. The subrange in which the etch depth is greater than 0 obtained when the hole is precisely etched and less than $S_1$ is displayed in yellow. The subrange in which the etch depth is greater than $S_1$ and less than $S_2$ is displayed in pink. The subrange in which the etch depth is greater than $S_2$ is displayed in red. The range of the residual film thickness in underetched area β is divided into two subranges, for example. The subrange in which the residual film thickness is between 0 and $S_3$ is displayed in blue. The subrange is which the residual film thickness is greater than $S_3$ is displayed in violet. Precise etching is displayed in green. Degrees of the inspected specimen are displayed in different colors indicating the subranges in which measured absorbed current values fall. Alternatively, the level indicative of precise etching may be indicated by 0. The three subranges within an overetched area may be indicated by +1, +2, and +3, respectively, from the lower side. The two subranges within an underetched area may be indicated by −1 and −2, respectively, from the higher side. In this way, degrees of etching may be indicated by numerical values indicating the levels of subranges in which measured absorbed current values fall. For example, the etch depth is X nm, or the remaining film thickness is Y nm.

A quite large number of contact holes exist over the whole one silicon wafer. If the contact holes are inspected one by one, an exorbitantly long time will be necessary. Accordingly, the whole wafer surface is appropriately divided into seven virtual portions. One contact hole in each portion is inspected as a typical contact hole. With this inspection, however, it is not certain whether the results of the inspection obtained from the inspected contact hole represent the state of many etched or developed contact holes existing close to the inspected hole. Furthermore, it is difficult to appropriately judge the development or etching step that is a previous process step only from the results of inspections of such few (seven) contact holes. Contact holes are not processed one by one but many holes in the whole semiconductor substrate are processed at a time by batch processing. For example, the degree of penetration of each hole is affected by the intensity distribution of plasma in a plasma etcher for etching contact holes or by variations in chemical reaction of a resist developing solution within the substrate. Therefore, it is quite meaningful to judge the overall state of the contact holes formed over the whole substrate rather than the state of each individual contact hole. Accordingly, another embodiment of the present invention is next described.

A substrate provided with a large number of contact holes and used for a semiconductor device is prepared. Small areas each containing plural contact holes are successively irradiated with a charged-particle beam. During each irradiation, the absorbed current flowing between the substrate and ground is measured. An absorbed current signal about each small area is obtained over the whole substrate. The measured absorbed current value is compared with the relation of the current flowing between the sample and ground to the degree of etching of the contact hole, the relation being previously found using a reference sample. Thus, the distribution of etching degrees over the whole substrate is obtained. This distribution makes it possible to grasp the overall state of the contact holes over the whole substrate surface. Preferably, the size and positions of the small areas are so set that plural contact holes are present within each small area. Where each small area having plural or numerous contact holes is entirely irradiated with a charged-particle beam and the resulting absorbed current is measured in this way, the amount of the resulting absorbed current is larger than where one contact hole is irradiated with the beam. During detection, problems of noise and response speed are alleviated. Furthermore, where only one contact hole is irradiated with an electron beam and this hole is formed peculiarly differently from many other surrounding contacts, it is not desirable to represent the overall state of the many surrounding contact holes by the results of the measurement on only the single contact hole. In contrast, where plural contact holes are present within each contact hole and all are irradiated with a charged-particle beam, then average results will be obtained. If a unique hole is contained among them, the effect can be modified greatly. The results are more preferable as measurement results representing the state of formed contacts within the region.

Figure 6:
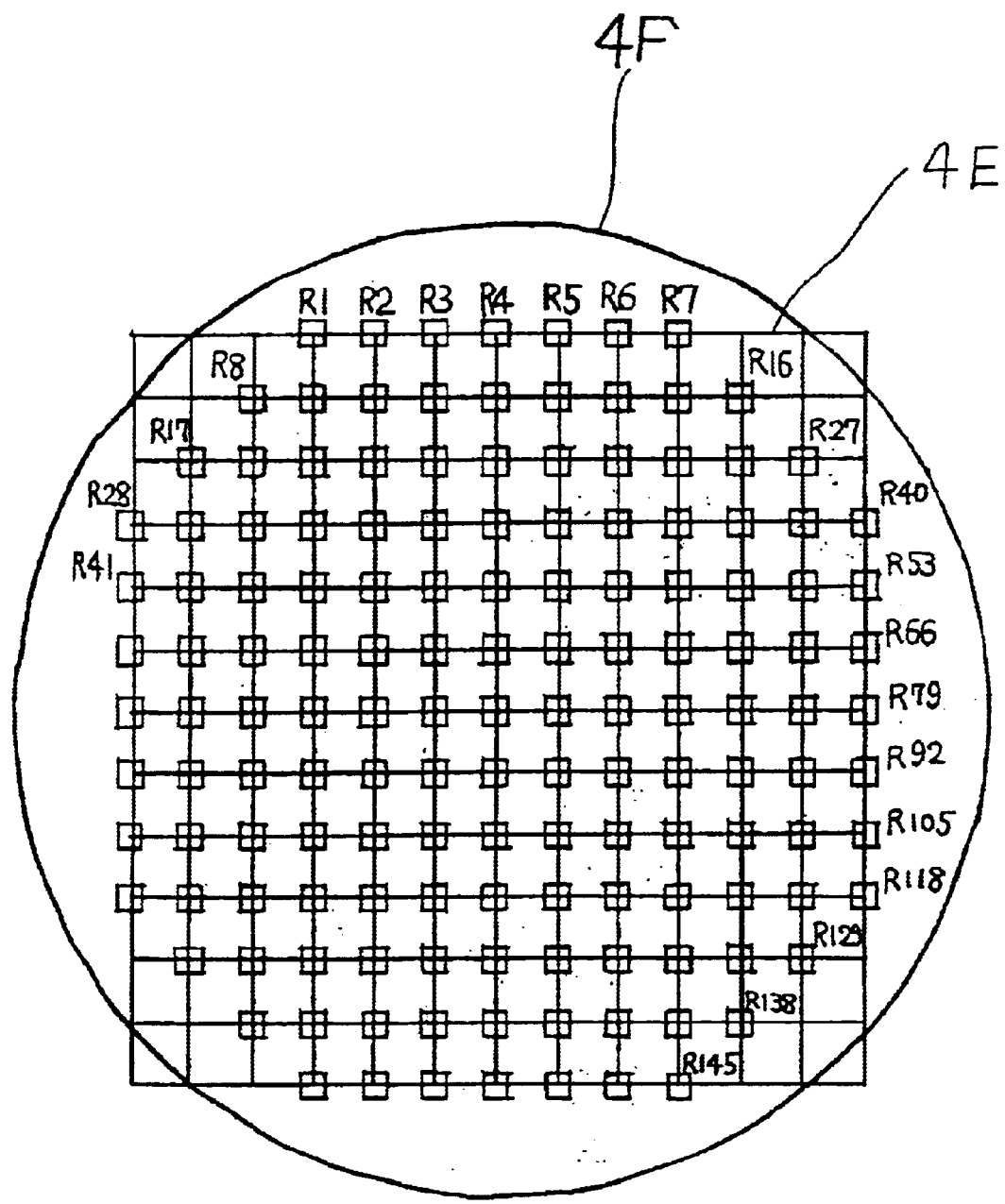
FIG. 6 is a view showing absorbed current measurement regions on the effective surface of a wafer sample surface.
Figure 7:
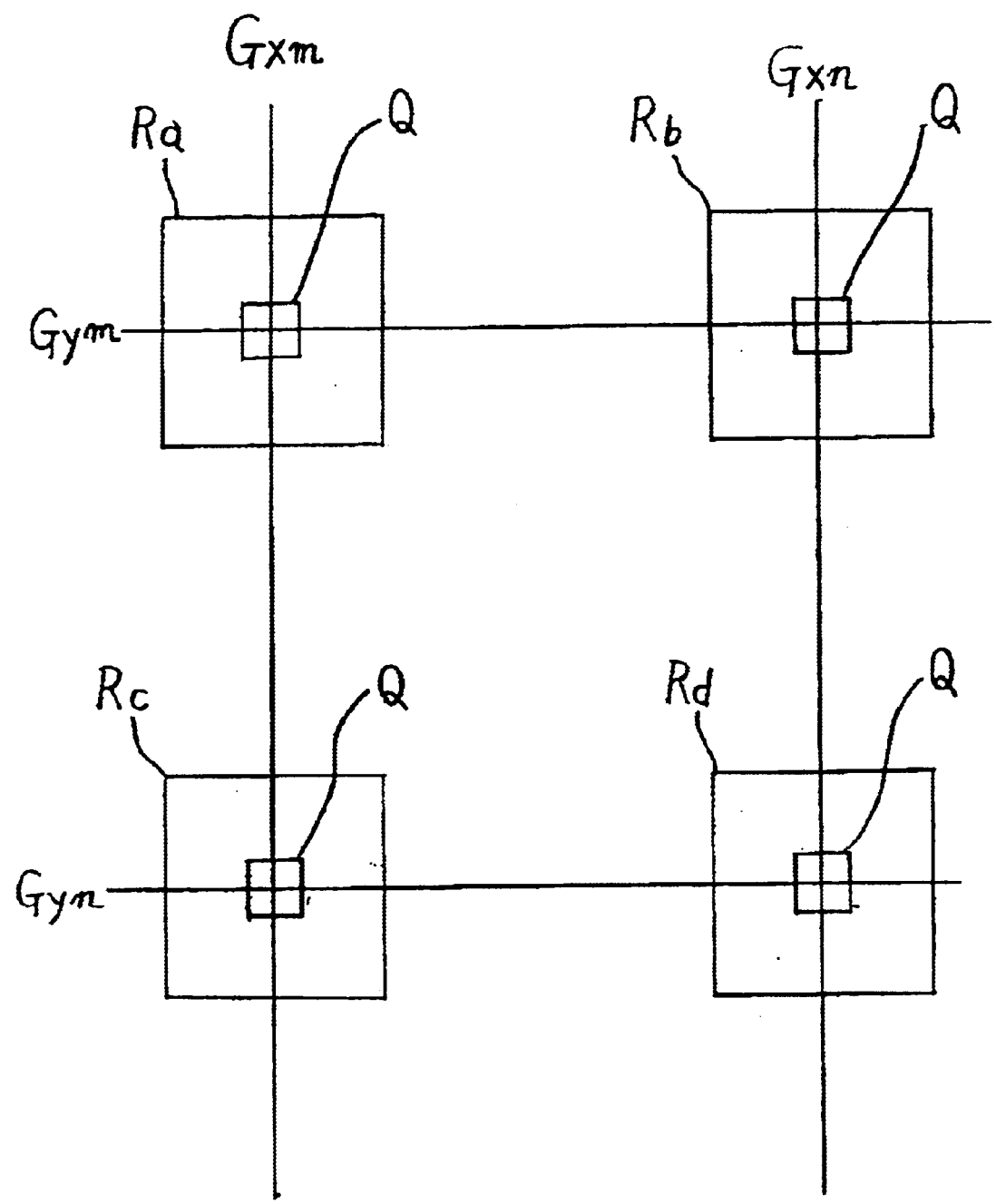
FIG. 7 is an enlarged view of parts of FIG. 6.

First, absorbed current measurement regions are established over the whole effective surface 4E of the surface of a sample 4F on which a semiconductor chip is fabricated. For example, 13 virtual horizontal lines spaced equally from each other and 13 virtual vertical lines spaced equally from each other are drawn perpendicular to each other on the effective surface 4E of the sample surface 4F, as shown in FIG. 6. A measurement region is established around each intersection of these lattice lines. Preferably, the measurement regions are uniform in number of contact holes and in their arrangement. The spacing between the lattice lines and their positions are so selected that the lattice points appear in locations created by the same location within one pattern (chip pattern) by repeatedly arraying this pattern. In FIG. 6, chip patterns for which measurement regions are established are indicated by R1, R2, R3, R4, R5, ..., R145. In practice, each region irradiated with an electron beam is set to a small area Q measuring from 1 mm×1 mm to 0.1 mm×0.1 mm, taking account of a scanning width of 1 mm in which deflection distortion of the electron beam is tolerated as shown in FIG. 7. A given number of contact holes are formed within this small area. In FIG. 7, Gxm, Gxn, Gym, and Gyn indicate lattice lines. Ra, Rb, Rc, and Rd are chip pattern areas corresponding to the above-described R1, R2, R3, R4, R5, ..., R145. Each small area Q is illuminated with an electron beam in the manner described below.

The excitation of the condenser lens system 2 and the excitation of the objective lens 3 are controlled by excitation signals from the lens control circuits 8 and 9. Thus, the convergence of the electron beam is adjusted so that the beam hitting the sample 4 is sharply focused onto it. The sample stage 7 is moved in steps by the stage drive mechanism 6 such that the centers of the small areas Q within the regions R1, R2, R3, R4, R5, ..., R145 arrive at the center (center of scanning of the electron beam) of the optical axis of the electron beam in succession. At this time, each small area Q is scanned once or plural times with the sharply focused electron beam while each small area Q is halted at the center of the optical axis of the beam. In this embodiment, the electron beam is sharply focused, and each small area Q is scanned. Alternatively, the cross-sectional shape of the electron beam may be made to correspond to the shape of each small area Q on the sample, and the whole small area may be kept illuminated for a given time.

The absorbed current flowing through the sample 4 is amplified by the current amplifier 16 while each small area Q is being scanned with the electron beam or totally illuminated with the electron beam. The amplified current is integrated or accumulated during the scanning period. The integrated absorbed current detected in this way contains information indicating the average result of formation of the plural contact holes within each small area Q (i.e., how the average contact hole has been formed).

Where resist is left within the contact holes or an unetched dielectric film remains, if an electron beam is directed to it, a charging effect will be produced. However, the effect will not be so serious that the absorbed current cannot be detected. Nonetheless, measurement of the absorbed current may be made impossible for other cause (i.e., a charging effect produced by the fact that the electron beam hits locations other than contact holes). Accordingly, when the electron beam is made to hit the sample 4, secondary electrons emitted by the sample 4 may be detected by a secondary electron detector (not shown) which is normally mounted in this instrument. A secondary electron image may be displayed on a display unit based on the results of the detection. This display unit may be the aforementioned display unit 19 or a separately mounted display unit. The charging effect on the sample 4 is judged from the image. Then, the probe current is determined. In this way, the charging effect on the sample 4 is reduced to a minimum, and noise on the distribution image displayed on the display unit 19 as described later is reduced.

In this manner, absorbed current signals obtained from the small areas Q within the chip patterns R1, R2, R3, R4, R5, . . . , R145 are successively sent to the control unit 15 via the A/D converter 17. The control unit 15 stores data items, 145 in total, about the absorbed current signals derived from the small areas Q at those addresses of the first memory 18A which correspond to the coordinates (positions) of the small areas Q.

Absorbed current values are previously measured using a reference sample under the same conditions (i.e., the same material, the same number of contact holes, and the same measurement conditions) as the small areas Q of the inspected sample. The relations of etch depth and remaining film thickness to the measurement current values are found. Based on the found relations, the range of absorbed currents is divided into six subranges as shown in FIG. 5. Six different colors or six brightness levels are assigned to the six subranges, respectively. The relations of the assigned colors or brightness levels to absorbed current values (FIG. 5) are stored in the second memory 18B.

Then, the control unit 15 reads 145 items of data about the absorbed current intensities over the whole sample surface from the memory 18A. An etch degree map is displayed on the viewing screen of the display unit 19 making use of the relations of the absorbed current value read from the second memory 18B to the assigned colors or brightness levels.

Figure 8:
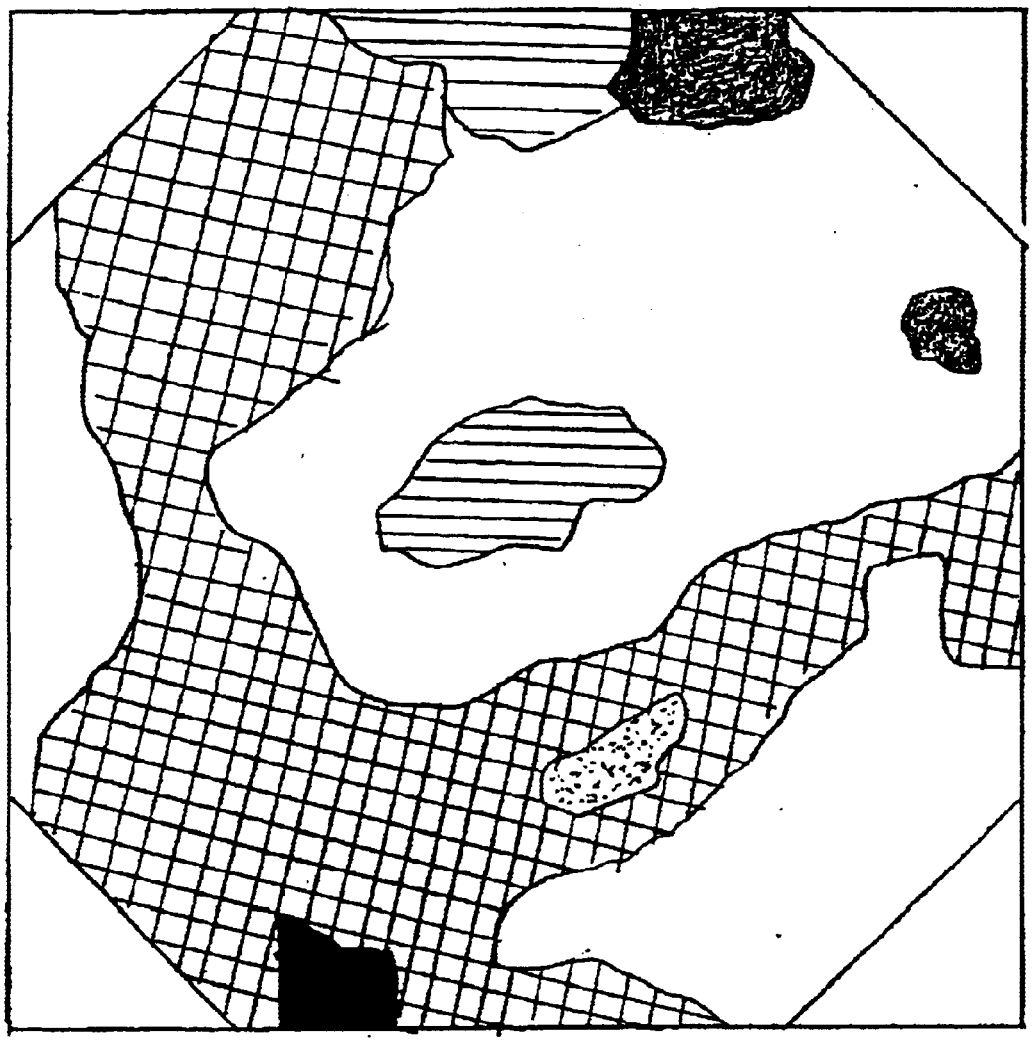
FIG. 8 is a contour map representation of the distribution of etching degrees over the whole sample displayed on the viewing screen of a display unit.
Figure 1A:
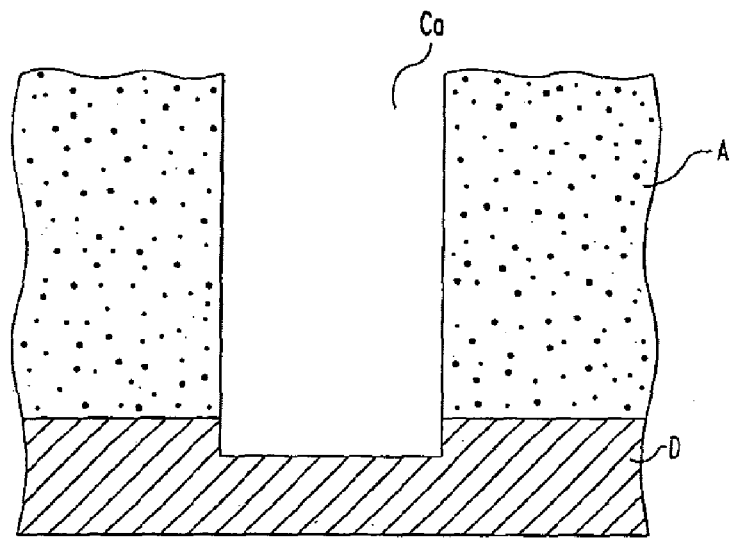
Figure 1B:
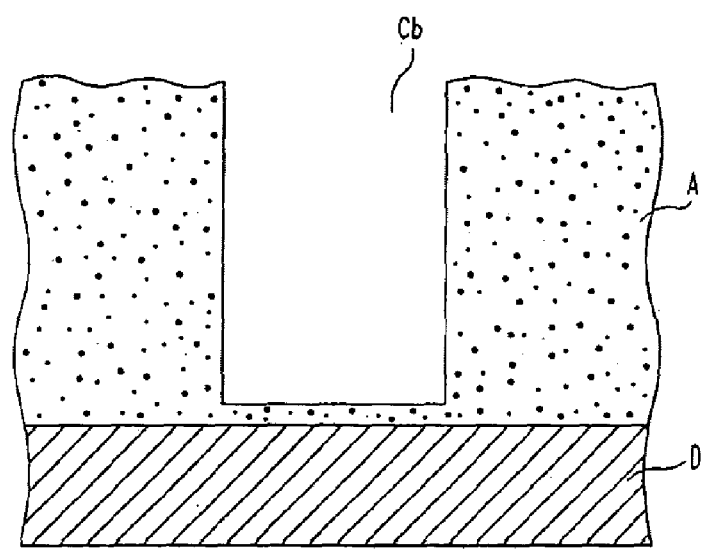

At this time, a lattice consisting, for example of 13×13 lattice lines is displayed on the viewing screen. A dot of an appropriate size determined taking account of the lattice spacing is displayed at each lattice position. The distribution of degrees of etching over the whole sample surface is displayed in terms of 145 dots by displaying each dot in a color or with a brightness corresponding to the degree of etching relative to the measured current intensity value at each lattice point. The displayed image is inevitably rough if it is displayed in terms of 145 dots representing lattice points. A finer map can be displayed by increasing the number of dots. This is accomplished by adding displayed points between the 145 dots by an interpolation method. FIG. 8 shows an example in which data about numerous points between lattice points is found using the above-described data by an interpolation method and the intervening points are displayed. The distribution of degrees of etching over the whole wafer sample is displayed on the viewing screen of the display unit 19 in terms of six colors or six brightness levels. This method of display is known as contour plot representation or contour representation.

In the above embodiment, an electron beam is made to hit a plurality of small regions having contact holes and previously established over the whole effective surface of a sample, such as a wafer. Values of the absorbed current are measured. Then, the distribution of degrees of etching over the whole sample is found. Therefore, one can reliably judge how contact holes are etched over the whole sample or in a portion of interest. That is, the tendency can be judged reliably.

Contour representation of the degrees of etching over the whole sample makes clear the degrees of etching among various portions of the sample. Consequently, one can appropriately judge the etching processing. Also, the representation is useful in judging which portion should be analyzed for defects in contact holes.

In the embodiment described above, an electron beam is directed to one small region of a chip pattern lying at one of the intersections of lattice lines, and the absorbed current is measured. Alternatively, the electron beam may be directed to plural small regions, and the resulting absorbed current may be measured.

Where each small region Q is scanned plural times, an integrated value obtained by each scan may be averaged. The average value may be used as a measurement value obtained from this region.

Furthermore, in the above embodiment, when locations at which the absorbed current is measured are established on the effective surface of a sample surface, 13 virtual horizontal lines and 13 virtual vertical lines are drawn at right angles to each other on a sample surface. The number of the lattice lines is not limited to the number used in this embodiment. If the number of lattice lines is increased to increase the number of measurement regions, then the accuracy of the distribution of degrees of etching over the whole sample will be enhanced. However, the number of measurements is increased accordingly. Conversely, if the number of lattice lines is reduced, the accuracy of the distribution will deteriorate but the number of measurements is reduce accordingly.

Figure 9:
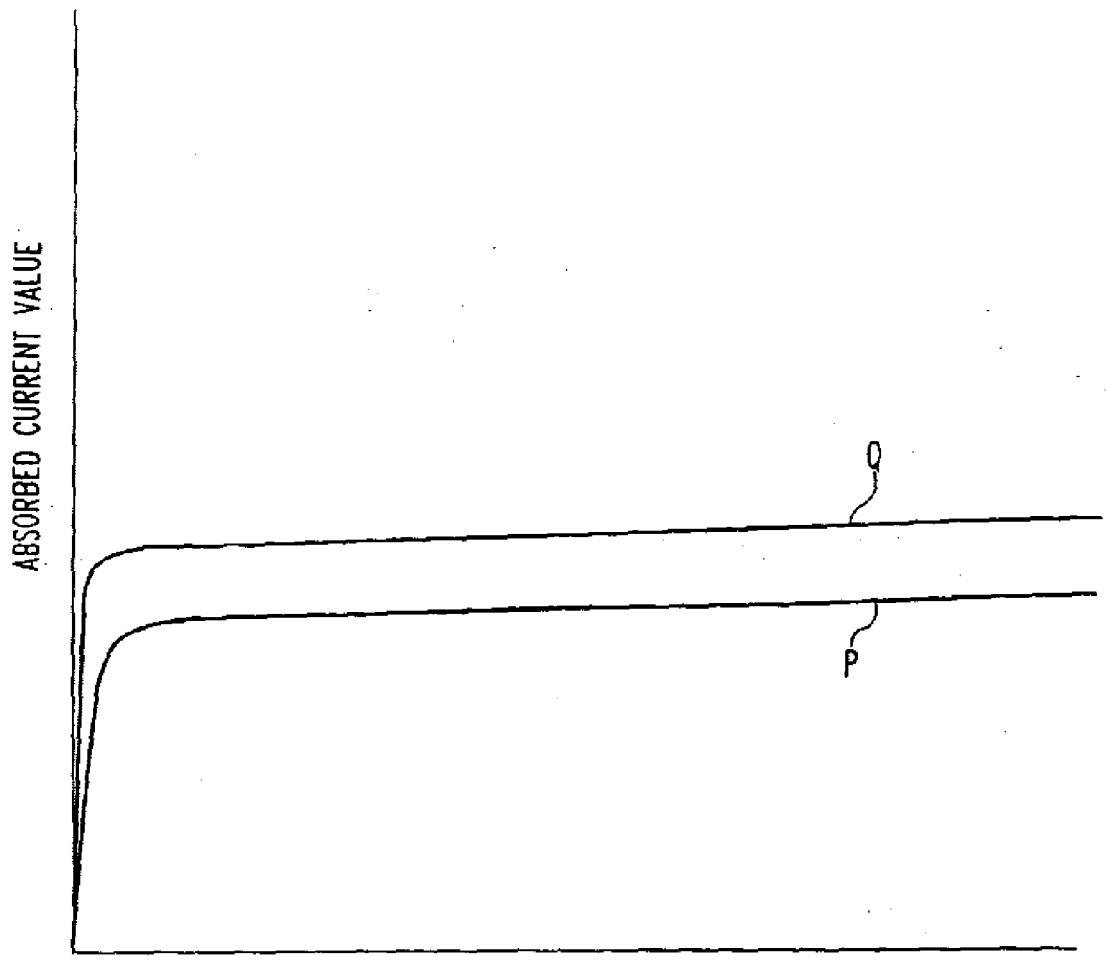
FIG. 9 is a graph showing the characteristics of a reference sample precisely etched and the characteristics of a sample to be inspected.

Another embodiment is now described. A sample to be investigated and a reference sample precisely etched are prepared. A charged-particle beam is directed to each region containing contact holes in each of the investigated sample and reference sample. The electric current flowing between the sample and ground is detected. This series of steps is repeated for previously set plural regions. Data about the current distributions on both samples is found. Graphs showing the current characteristics of the regions of the inspected sample and the precisely etched reference sample are displayed side by side on the display unit 19 as shown in FIG. 9. The graph of FIG. 9 is obtained by plotting detected current values indicating measurement values obtained from various regions. The current values are arrayed in order such that the smallest value is at the left end. Curve P indicates that characteristics of the reference sample, showing the manner that it is precisely etched. Curve Q indicates the characteristics of the inspected sample. Comparison of these characteristic curves makes it possible to judge how the inspected sample is etched. In this case, as the difference of the characteristic curve Q of the inspected sample with the characteristic curve P of the precisely etched reference sample decreases, the inspected sample is etched better.

In the embodiments described above, electron beam irradiation is utilized. Instead, ion beam irradiation may also be used.

Having thus described our invention with the detail and particularity required by the Patent Laws, what is desired protected by Letters Patent is set forth in the following claims.

The invention claimed is:

1. A method of finding the depth of a hole in an etched layer in a semiconductor substrate sample using a charged-particle beam, comprising the steps of:

irradiating the hole with the charged-particle beam;

detecting an electric current flowing between the substrate sample and ground as a result of the irradiation; and finding the etch depth of said hole in the substrate sample, based on a previously found relation of the current flowing between holes in a reference sample and ground to the depths of holes in said reference sample.

2. A method of inspecting a hole in an etched layer in a semiconductor substrate sample using a charged-particle beam, comprising the steps of:

irradiating the hole with the charged-particle beam;

detecting an electric current flowing between the inspected sample and ground as a result of the irradiation; and finding how the hole in the inspected sample is etched, based on previously found relations of the current flowing between holes in a reference sample and ground to remaining film thickness in the holes in said reference sample.

3. A method of finding the depth of a hole as set forth in claim 1, further including the steps of:

previously finding a relation of electric current flowing between the reference sample and ground to etch depths of holes into the substrate, using the reference sample;

previously classifying these etch depths into plural groups; and finding to which of the groups the currently inspected etch depth belongs, based on the detected electric current flowing between the inspected sample and ground.

4. A method of inspecting a hole as set forth in claim 2, further including the steps of:

previously finding a relation of electric current flowing between the reference sample and ground to etch depths of holes or a relation of electric current flowing between the reference sample and ground to remaining film thicknesses in the holes;

previously classifying these etch depths or remaining film thicknesses into plural groups; and finding to which of the groups the currently inspected etch depth belongs, based on the detected electric current flowing between the inspected sample and ground.

5. A method of inspecting a hole using in an etched layer in a semiconductor substrate sample a charged-particle beam, comprising the steps of:

irradiating the hole with the charged-particle beam;

detecting an electric current flowing between the inspected substrate sample and ground as a result of the irradiation;

comparing the detected electric current with an electric current that is previously found using a reference sample flowing between the reference sample and ground where the hole is precisely etched; and judging that the hole in the inspected sample is precisely etched if the two currents agree, that the hole is overetched if the detected electric current is greater than the previously found current, and that the hole is underetched if the detected current is smaller than the previously found current.

6. A method of finding the depths of holes in an etched layer in a semiconductor substrate sample using a charged-particle beam, comprising the steps of:

irradiating a region containing the holes with the charged-particle beam;

detecting an electric current flowing between the inspected sample and ground as a result of the irradiation;

repeating these steps for plural regions previously established on the inspected sample;

obtaining data about a distribution of etch depths of the holes in the inspected sample in the substrate, based on the detected current and on a previously found relation of detected current flowing between the reference sample and ground to etch deaths of the holes into the substrate; and displaying a map based on the obtained data about the distribution of etched depths on a display unit.

7. A method of inspecting holes using a charged-particle beam as set forth in claim 6, wherein said map is displayed with different symbols, in different colors, or with different brightness levels.

8. A method of inspecting holes using a charged-particle beam as set forth in claim 7, wherein said different symbols are characters.

9. A method of finding the depths of holes in an etched layer in a semiconductor substrate sample using a charged-particle beam, comprising the steps of:

irradiating a region containing the holes with the charged-particle beam;

detecting an electric current flowing between the inspected sample and ground as a result of the irradiation;

repeating these irradiating and detecting steps for plural regions previously established on the inspected sample;

obtaining data about a distribution of etch depths of the holes in the inspected sample in the substrate, based on the detected current and on a previously found relation of electric current flowing between a reference sample and ground to etch depths of the holes into the substrate and also on a previously found relation of the electric current flowing between the reference sample and ground to remaining film thicknesses in the holes; and displaying a map on a display unit, based on data obtained about the distribution of degrees of etching in the holes in the inspected sample.

10. A method of inspecting holes using a charged-particle beam as set forth in claim 9, wherein said map is displayed with different symbols, in different colors, or with different brightness levels.

11. A method of inspecting holes using a charged-particle beam as set forth in claim 10, wherein said different symbols are characters.

12. A method of inspecting holes using a charged-particle beam as set forth in any one of claims 9–11, wherein each of said plural regions is so selected that plural holes are contained therein.

13. A method of inspecting holes using a charged-particle beam as set forth in any one of claims 9–11, wherein said plural regions illuminated with said charged-particle beam are selected to be in certain positions within a periodic pattern formed on said sample.

14. A method of inspecting holes using a charged-particle beam as set forth in any one of claims 9–11, wherein each of said plural regions is totally scanned with said charged-particle beam in a scanning period, said electric current is accumulated during the scanning period, and an obtained accumulated value is used as a measurement value about each region.

15. A method of inspecting holes using a charged-particle beam as set forth in any one of claims 9–11, wherein each of said plural regions is totally scanned with said charged-particle beam in a scanning period, an average value of said current over the scanning period is taken, and said average value is used as a measurement value about each region.

16. A method of inspecting holes using a charged-particle beam as set forth in any one of claims 9–11, wherein each of said plural regions is totally irradiated with said charged-particle beam without scanning of the beam in an irradiation period, said electric current is accumulated during the irradiation period, and an obtained accumulated value is used as a measurement value about each region.

17. A method of inspecting holes using a charged-particle beam as set forth in any one of claims 9–11, wherein each of said plural regions is totally irradiated with said charged-particle beam without scanning of the beam in an irradiation period, an average value of said current over the irradiation period is taken, and said average value is used as a measurement value about each region.

18. A method of inspecting holes using a charged-particle beam, comprising the steps of:

preparing a reference sample precisely etched;

preparing an unknown sample that is not known whether it has been etched precisely or not;

irradiating a region of said reference sample containing holes with the charged-particle beam;

detecting an electric current flowing between the reference sample and ground;

repeating these irradiating and detecting steps for plural preselected regions on said reference sample;

irradiating a region of said unknown sample containing holes with the charged-particle beam;

detecting an electric current flowing between the unknown sample and ground;

repeating these irradiating and detecting steps for plural preselected regions on said unknown sample;

finding data about current distributions on the reference sample and on the unknown sample;

creating graphs indicative of the characteristics of the currents flowing through the regions of the reference sample and unknown sample; and displaying said graphs side by side on a display unit.

19. A method of inspecting holes using a charged-particle beam as set forth in claim 18, wherein said graphs indicative of the characteristics are formed by plotting detected current values in increasing order, from their minimum values.

20. A method of inspecting holes using a charged-particle beam as set forth in claim 18, wherein said graphs indicative of the characteristics are formed by plotting detected current values in decreasing order, from their maximum values.

* * * * *

UNITED STATES PATENT AND TRADEMARK OFFICE
CERTIFICATE OF CORRECTION

PATENT NO. : 6,787,770 B2
DATED : September 7, 2004
INVENTOR(S) : Kikuchi et al.

It is certified that error appears in the above-identified patent and that said Letters Patent is hereby corrected as shown below:

Replace Informal drawings submitted January 30, 2002 with formal drawings submitted August 2, 2002.

Column 12,
Line 24, "deaths of the holes" should read -- depths of the holes --

Signed and Sealed this

Nineteenth Day of April, 2005

JON W. DUDAS
*Director of the United States Patent and Trademark Office*

|  RED |  GREEN |
|  PINK |  BLUE |
|  YELLOW |  VIOLET |